(12) United States Patent
Alhalabi

(10) Patent No.: US 12,324,865 B2
(45) Date of Patent: Jun. 10, 2025

(54) AUTOMATED GERMICIDAL INHIBITOR SYSTEM AND METHOD OF OPERATION

(71) Applicant: Bassem Alhalabi, Boca Raton, FL (US)

(72) Inventor: Bassem Alhalabi, Boca Raton, FL (US)

( * ) Notice: Subject to any disclaimer, the term of this patent is extended or adjusted under 35 U.S.C. 154(b) by 686 days.

(21) Appl. No.: 16/942,138

(22) Filed: Jul. 29, 2020

(65) Prior Publication Data

US 2022/0031893 A1    Feb. 3, 2022

(51) Int. Cl.
*A61L 2/24*      (2006.01)
*A61L 2/10*      (2006.01)
*A61L 2/22*      (2006.01)

(52) U.S. Cl.
CPC ..................... *A61L 2/24* (2013.01); *A61L 2/10* (2013.01); *A61L 2/22* (2013.01); *A61L 2202/14* (2013.01); *A61L 2202/15* (2013.01); *A61L 2202/24* (2013.01)

(58) Field of Classification Search
CPC ..... A61L 2/24; A61L 2/10; A61L 2/22; A61L 2202/14; A61L 2202/15; A61L 2202/24; A61L 2202/25
See application file for complete search history.

(56) References Cited

U.S. PATENT DOCUMENTS

| | | | |
|---|---|---|---|
| 6,879,263 B2 * | 4/2005 | Pederson | B60Q 1/2696 345/82 |
| 9,675,720 B2 * | 6/2017 | Romo | A61L 9/20 |
| 2010/0327766 A1 * | 12/2010 | Recker | H02J 50/40 362/20 |
| 2011/0121654 A1 * | 5/2011 | Recker | H05B 45/3725 307/64 |
| 2014/0276375 A1 * | 9/2014 | Minkus | A61M 1/1682 705/2 |
| 2015/0367008 A1 * | 12/2015 | Romo | A61L 9/20 250/492.1 |
| 2019/0374075 A1 * | 12/2019 | Barnett | A61L 2/10 |
| 2021/0369015 A1 * | 12/2021 | Nevitt | A61L 2/10 |

* cited by examiner

*Primary Examiner* — Regina M Yoo
(74) *Attorney, Agent, or Firm* — Edison Law Group; Daniel Polk

(57) ABSTRACT

An automated ultraviolet germicidal system sterilizes a sterilization area with an automated sterilization mechanism that is selectively actuated and terminated, depending on events in the sterilization area, and elapse of a predetermined time period. A sterilization mechanism selectively emits a germicide element in or near a sterilization area, so as to sterilize the sterilization area from germs. An actuation device operatively connects with the sterilization mechanism to regulate the actuation and termination of the germicide element generated by the sterilization mechanism. A command device, controlled by a user, transmits an actuation signal to the actuation device to actuate the sterilization mechanism, upon entry of a code. A termination device has a set of sensors that detects events near the sterilization area, and transmits a termination signal to the actuation device to terminate operation of the sterilization mechanism upon detection of the event, or after elapse of time period.

17 Claims, 3 Drawing Sheets

AUTOMATED GERMICIDAL INHIBITOR SYSTEM AND METHOD OF OPERATION

FIELD OF THE INVENTION

The present invention relates generally to an automated germicidal inhibitor system and method of operation. More so, the present invention relates to an automated germicidal inhibitor system that provides a sterilization mechanism to selectively emit a germicide element in and around a sterilization area, so as to sterilize the sterilization area from germs; whereby an actuation device operatively connects with the sterilization mechanism to regulate the actuation and termination of the germicide element generated by the sterilization mechanism; whereby a command device, controlled by a user, transmits a signal to the actuation device to actuate the sterilization mechanism, upon entry of a code by the user; and whereby a termination device has a set of sensors that detect at least one event at or near the sterilization area, and transmits a signal to the actuation device to terminate operation of the sterilization mechanism upon detection of the event, or after elapse of a predetermined time period.

BACKGROUND OF THE INVENTION

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

Short wavelength ultra violet light is known in the art to be efficacious for sterilization of an enclosed area. Ultraviolet light is usually produced artificially by electric-arc lamps. Ultra violet light is a high frequency wavelength of light within the ultraviolet band and has been shown to be the most bactericidal type of ultraviolet light. This ultra violet light has wavelengths of about 2800 Å to 150 Å. Such short-wavelength ultra violet light kills microorganisms by destroying their nucleic acids and disrupting their DNA, leaving them unable to perform vital cellular functions.

Generally, ultra violet light radiation is used to sterilize/disinfect areas, such as: hospitals, nurseries, operating rooms, cafeterias and to sterilize vaccines, serums, toxins, municipal waste, and drinking waters. Such ultra violet light radiation can be utilized in an operating room environment to help sterilize contaminations from a variety of sources including infected equipment brought in, the surgical patient, the surgical team, and outside air.

Other proposals have involved systems to sterilize an enclosed area with ultra violet light. The problem with these sterilization techniques is that they do not power off when a situation is dynamically created where the UV light may impose harm in the enclosed area, such as sudden human presence or sudden change in the surrounding environment beyond an acceptable level, which constitutes a safety hazard. Also, other systems may not have a timer to automate powering off the sterilization ultra violet lights. Even though the above cited systems to sterilize an enclosed area with ultra violet light meet some of the needs of the market, an automated germicidal inhibitor system that provides a sterilization mechanism to selectively emit a germicide element in and around a sterilization area, so as to sterilize the sterilization area from germs; whereby an actuation device operatively connects with the sterilization mechanism to regulate the actuation and termination of the germicide element generated by the sterilization mechanism; whereby a command device, controlled by a user, transmits a signal to the actuation device to actuate the sterilization mechanism, upon entry of a code by the user; and whereby a termination device has a list of sensors that detects at least one event at or near the sterilization area, and transmits a signal to the actuation device to terminate operation of the sterilization mechanism upon detection of the event, or after elapse of a predetermined time period, is still desired.

SUMMARY

Illustrative embodiments of the disclosure are generally directed to an automated ultraviolet germicidal system and method of operation. The automated ultraviolet germicidal system serves to sterilize a sterilization area with an automated sterilization mechanism that is selectively actuated and terminated, depending on events in the sterilization area, and elapse of a predetermined time period.

In some embodiments, the automated germicidal inhibitor system provides a sterilization mechanism that selectively emits a germicide element in or near a sterilization area, so as to sterilize the sterilization area from germs. An actuation device operatively connects with the sterilization mechanism to regulate the actuation and termination of the germicide element generated by the sterilization mechanism. A command device, controlled by a user, transmits a signal to the actuation device to actuate the sterilization mechanism, upon entry of a code by the user. A termination device has a sensor that detects at least one event at or near the sterilization area, and transmits a signal to the actuation device to terminate operation of the sterilization mechanism upon detection of the event, or after elapse of a predetermined time period.

In one aspect, an automated germicidal inhibitor system, comprises a sterilization mechanism operable to emit a germicide element.

The automated germicidal inhibitor system further comprises an actuation device detachably coupled to the sterilization mechanism, the actuation device comprising a plug operable to enable coupling to an external power outlet, whereby energy from the power outlet powers the sterilization mechanism.

The actuation device further comprising an actuation transreceiver and a switch mechanism, the actuation transreceiver and the switch mechanism being operatively connected to the sterilization mechanism, the switch mechanism operable to actuate operation of the sterilization mechanism.

The automated germicidal inhibitor system further comprises a command device comprising a command transceiver, an entry key pad, and a microcontroller, the entry key pad operable to enable entry of a code, the microcontroller operable to count a predetermined time period, the command transreceiver operable to transmit an actuation signal to the actuation transreceiver of the actuation device when the code is entered, whereby the actuation signal commands the switch mechanism to actuate operation of the sterilization mechanism.

The automated germicidal inhibitor system further comprises one or more termination devices comprising a termination transreceiver and a set of sensors, the sensors operable to detect an undesirable event or events, the sensor transreceiver operable to transmit a termination signal to the actuation transreceiver of the actuation device when the event is detected, or when the predetermined time period elapses, or both. Whereby the termination signal commands the switch mechanism of the actuation device to terminate operation of the sterilization mechanism.

In another aspect, the sterilization mechanism comprises an ultraviolet light tube.

In another aspect, the germicide element comprises a short-wavelength ultraviolet light.

In another aspect, the sterilization mechanism comprises a germicide sprayer.

In another aspect, the germicide element comprises a sanitization composition.

In another aspect, the plug comprises an electrical plug.

In another aspect, the switch mechanism includes at least one of the following: a static bypass switch, a maintenance bypass switch, UPS-mounted bypass switch, and an electrical bypass switch.

In another aspect, the switch mechanism comprises a bypass socket.

In another aspect, all of: the actuation device, the command device, and the sensor device, comprise a microcontroller, such as a PIC or MSP microcontroller.

In another aspect, the actuation transreceiver comprises a radio frequency module operable to enable wireless reception of the actuation signal and the termination signal.

In another aspect, the actuation device comprises an audible alert mechanism.

In another aspect, the actuation device comprises a digital display operable to display entry of the code into the key pad.

In another aspect, the signals comprise a radio frequency signal.

In another aspect, the code is a password, memorized by the user, or given to the user by a larger entity.

In another aspect, the predetermined time period is about 20 minutes by default, but it is also user programmable.

In another aspect, the event includes at least one of the following: motion, noise, temperature, and light sensors.

In another aspect, the event occurs when at least one of: the motion, the noise, the temperature, and the light, exceed an event threshold.

In another aspect, the event occurs when at least one of: the motion, the noise, the temperature, and the light, exceed the event threshold by about 5%, or any other user programmable threshold percentage.

In another aspect, the sterilization mechanism is operable to emit a germicide element in or near a sterilization area.

In another aspect, the sterilization area includes at least one of the following: a hospital operating room, a waiting area at a bus station, and a public restroom.

One objective of the present invention is to automate the sanitization of an area with short-wavelength ultraviolet light.

Another objective is to allow a user to control the actuation of the ultraviolet light through entry of a password.

Yet another objective is to actuate the ultraviolet light after a predetermined time period has lapsed.

An exemplary objective is to provide a sensor device that detects human activities in the area, and cause the inhibitor device to transit a signal to the actuation device to terminate the ultra violate radiation.

Additional objectives are to terminate the sanitization when a person enters the area, or the temperature, light, and noise level changes.

Additional objectives are to provide an inexpensive to manufacture automated germicidal inhibitor system.

Additional objectives are to provide an easy to operate automated germicidal inhibitor system.

Other systems, devices, methods, features, and advantages will be or become apparent to one with skill in the art upon examination of the following drawings and detailed description. It is intended that all such additional systems, methods, features, and advantages be included within this description, be within the scope of the present disclosure, and be protected by the accompanying claims and drawings.

BRIEF DESCRIPTION OF THE DRAWINGS

The invention will now be described, by way of example, with reference to the accompanying drawings, in which.

Like reference numerals refer to like parts throughout the various views of the drawings.

DETAILED DESCRIPTION OF THE INVENTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper," "lower," "left," "rear," "right," "front," "vertical," "horizontal," and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Specific dimensions and other physical characteristics relating to the embodiments disclosed herein are therefore not to be considered as limiting, unless the claims expressly state otherwise.

An automated germicidal inhibitor system 100 and method of operation is referenced in FIGS. 1-5. The automated germicidal inhibitor system 100, hereafter "system 100", comprises a sterilization mechanism 106 that is configured to selectively emit a germicide element 108 at or near a sterilization area 102, based on user commands; and then terminate the emission of germicide element 108 upon detection of an event or after an elapsed time period. This utility of automation for sterilizing a sterilization area 102 enables a germicide element 108 to be emitted when the sterilization area 102 is void of hot-blooded animals activities such as humans motion or animal loud noises; and then terminated upon detection of such activities in the sterilization area 102. Such selective sterilization works to enhance safety for humans, so as not to allow any humans to be in contact with the germicide element 108.

Figure 1:
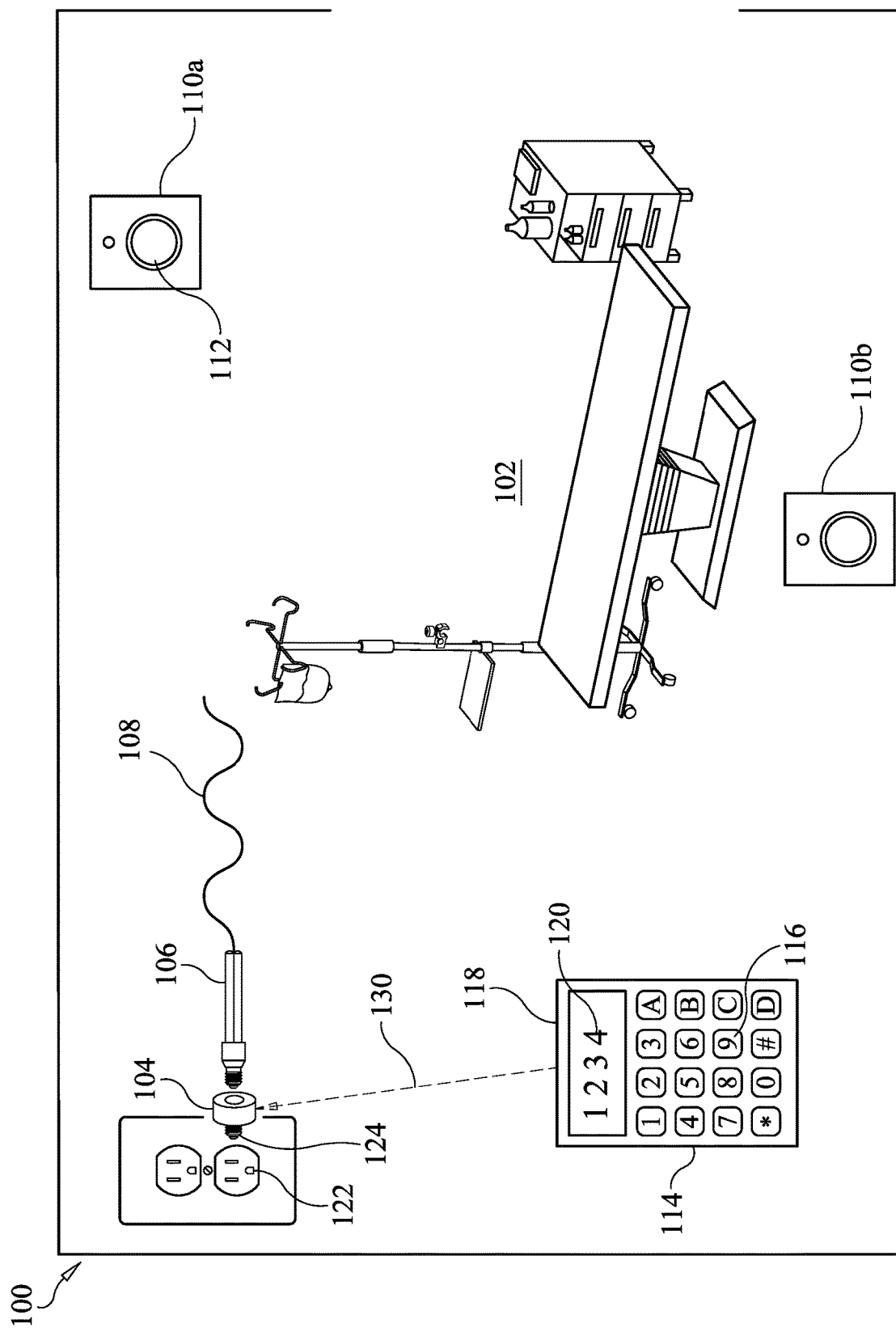
FIG. 1 illustrates a block diagram of an exemplary automated germicidal inhibitor system, showing a sterilization mechanism operationally actuated, in accordance with an embodiment of the present invention.

For example, FIG. 1 illustrates a block diagram of the system 100, showing a sterilization mechanism 106 operationally actuated. Conversely, FIG. 2 references the system 100 with the sterilization mechanism 106 operationally terminated upon detection of an event 126, i.e., a person entering the sterilization area 102. An elapsed period of time may also terminate operation of the sterilization mechanism 106.

Those skilled in the art will recognize that the sterilization area 102 can include a hospital operating room, a waiting area 102 at a bus station, and a public restroom. These are enclosed areas that often require sterilization against germs, such as viruses, bacteria, protozoa, and fungus. Thus, sterilization mechanism 106 emits the germicide element 108 on, near, or in the proximity of the sterilization area 102. As discussed below, various types of sterilization mechanisms and germicide elements may be used with the system 100.

To activate sterilization means, the system 100 comprises an actuation device 104 that detachably couples, and provides the mechanical articulations necessary to actuate the sterilization mechanism 106 for emitting the germicide element 108. In some embodiments, the sterilization mechanism 106 comprises an ultraviolet light tube, which is configured to emit a short-wavelength ultraviolet light throughout the sterilization area 102. The short-wavelength ultraviolet light may be a form of electromagnetic radiation with wavelength from 10-400 nm. However, the short-wavelength ultraviolet light is known in the art to be dangerous people and animals; and thus, it is advantageous automate termination of the short-wavelength ultraviolet light to power off, when people or animals are in the sterilization area 102.

In yet other embodiments, the sterilization mechanism 106 comprises a germicide sprayer that discharges a sanitization composition. The sanitization composition may include, without limitation, quaternary ammonium compounds, formaldehyde, glutaraldehyde, hydrogen peroxide, sodium hypochlorite, and other sanitizing agents known in the art. Similar to the ultraviolet light, the sanitization composition can include a spray with toxic ingredients that is harmful to people or animals. Thus, it is advantageous automate termination of the sanitization composition to stop discharging, when people or animals are in the sterilization area 102. In yet other embodiments, the system 100 utilizes any sterilization mechanism 106 and germicide element 108 known in the art.

To power the sterilization mechanism 106, the actuation device 104 comprising a plug 124 that couples to an external power outlet 122. The plug 124 may include an electrical plug that goes to an electrical outlet. External, whereby power outlet powers the sterilization mechanism 106. In alternative embodiments, the plug 124 couples to a source for compressed air or high-pressure fluids. And thus, it is through pneumatic means that the sterilization mechanism 106 is powered. However, depending on the type of sterilization mechanism 106, the power source is determined.

Figure 3:
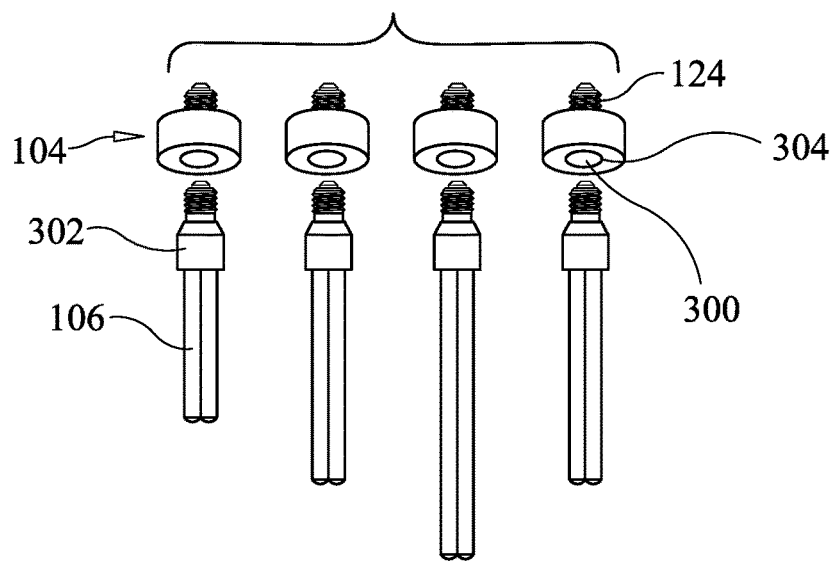
FIG. 3 illustrates a perspective view of an exemplary actuation device coupled to a sterilization mechanism, in accordance with an embodiment of the present invention.

Looking now at FIG. 3, the actuation device 104 further comprising an actuation transreceiver 302 and a switch mechanism 304. The actuation transreceiver 302 and the switch mechanism 304 are operatively connected to the sterilization mechanism 106. The actuation transreceiver 302 is configured to send and receive actuation signals 130 that command operation of the sterilization mechanism 106. In one possible embodiment, the actuation transreceiver comprises a radio frequency module operable to enable wireless reception of an actuation signal 130, and a termination signal 132. The signals 130, 132 may include radiofrequency signals known in the art. However other digital, or satellite signals may also be used, including data packets.

The switch mechanism 304 is configured to actuate operation of the sterilization mechanism 106. Thus, the switch mechanism converts the actuation signal 130 into a mechanical articulation. In one possible embodiment, the switch mechanism comprises a bypass socket. The bypass socket may plug directly into the external power outlet. However, in other embodiments, the switch mechanism may include, without limitation, a static bypass switch, a maintenance bypass switch, UPS-mounted bypass switch, and an electrical bypass switch.

In some embodiments, the actuation device 104 comprises an audible alert mechanism 300. The audible alert mechanism 300 can emit a beeping sound to indicate actuation or termination of the sterilization mechanism 106, as described below. In other embodiments, the actuation device 104 comprises a digital display 118 that is configured to display entry of the code 120 into the key pad 116. In one embodiment, the code 120 is a password that is used and known by the user, or provided to the user from an entity. In one non-limiting embodiment, the actuation device 104 comprises an MSP430 microcontroller. However, in other embodiments different microcontrollers or processors may also be used with the actuation device 104.

In one non-limiting embodiment, the switch mechanism 304 is a socket by-pass that is plugged into a normal household light socket, and any standard UV light tube is plugged into it. In one possible embodiment, the function of the switch mechanism for the actuation device 104 is to switch power on/off on UV light tubes. The actuation device 104 receives radio frequency signals form a command device 114 to turn on, and a different radio frequency signal from an inhibitor device 110*a* to pause the power. Several of the ultra violet light bulbs (or larger sizes) can be installed in a sterilization area 102, including a large room such as a hospital operating room, or a waiting area at a bus station. A single actuation device 104 may also be installed in smaller area such as a single public bathroom.

Figure 4:
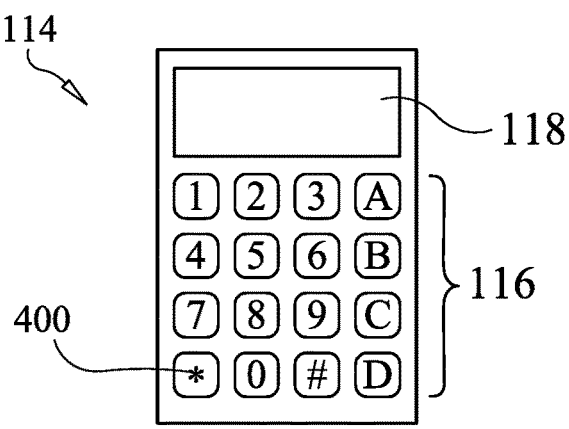
FIG. 4 illustrates a perspective view of an exemplary command device, in accordance with an embodiment of the present invention.

As referenced in FIG. 4, the system 100 further comprises a command device 114 that is the primary device used to initiate actuation of the sterilization mechanism 106. The command device 114 is in communication with the actuation device 104, and a termination device, described below. In one non-limiting embodiment, the command device 114 comprises an MSP430 microcontroller. However, in other embodiments different microcontrollers or processors may also be used with the command device 114. The command device 114 can be controlled directly by the user, or indirectly through a personal communication device in the hands of the user.

In some embodiments, the command device 114 may include a command transceiver, an entry key pad 116, and a microcontroller 400. The entry key pad 116 is configured to enable entry of a code 120. The entry keypad may have various alphanumeric digits arranged for entry into a processor that resides in the command device 114 to process the code 120. In one non-limiting embodiment, the code 120 is a password, which is memorized, or assigned to the user. The digital display 118 is also provided to show the user's entry of the code 120 into the entry key pad 116.

The microcontroller 400 is operable to count the predetermined time period. The predetermined time period may be 20 minutes. However, in other embodiments, the predetermined time period is greater or lesser than 20 minutes. In some embodiments, the command transreceiver transmits an actuation signal to the actuation transreceiver of the actuation device 104 when the code 120 is entered; transmits an inhibitor signal 132 when the predetermined time period elapses. For example, after 20 minutes, the sterilization mechanism 106 powers off, whether an event 126 occurs, or not. However, if an event 126 occurs before the 20-minute time period, the sterilization mechanism 106 powers off powers off in response to the generated termination signal 132.

For example, the user enters a code 120 directly into the command device 114, or indirectly through a personal mobile communication device. The code 120 is processed and transmitted wirelessly to the actuation transreceiver. This triggers the switch mechanism to actuate the sterilization mechanism 106. Such as, powering on the ultraviolet light source, or spraying the germicidal composition into the sterilization area 102. In essence, the actuation signal 130 commands the switch mechanism to actuate operation of the sterilization mechanism 106.

In one non-limiting embodiment, the command device 114 comprises a standalone handheld operating device with a radio frequency transceiver. The command device 114 has a keypad and a digital display 118. The function of the command device 114 is to transmit a radio frequency command to the actuation device 104 to turn on the ultra violet light tubes based on a successful password entry and an allowable time table. Only one command device 114 is needed for a complete system 100. The same command device 114 can be used to operate multiple systems, for example in different rooms. The command device 114 is programmed to work only the system that is paired with. For example, in a typical hospital, each floor uses one command device 114, which works only with multiple ultra violet lights on the same floor, where each system 100 has multiple actuator devices 104 and multiple inhibitor devices 110a, 110b, 110c.

Figure 5:
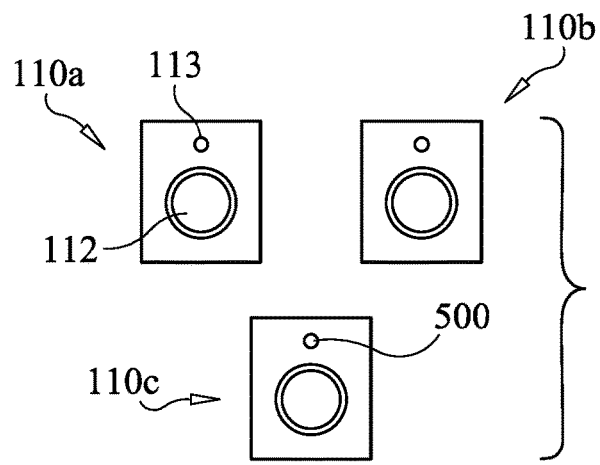
FIG. 5 illustrates a perspective view of exemplary termination devices, in accordance with an embodiment of the present invention.

Looking at FIG. 5, the system 100 also provides one or more termination devices 110a, 110b, 110c that work to terminate operation of the sterilization mechanism 106. The termination devices 110a-c are in operational communication with the command device 114 and the actuation device 104. In one non-limiting embodiment, the termination devices 110a-c comprise an MSP430 microcontroller. However, in other embodiments, different microcontrollers or processors may also be used with the termination device 110a-c.

Figure 2:
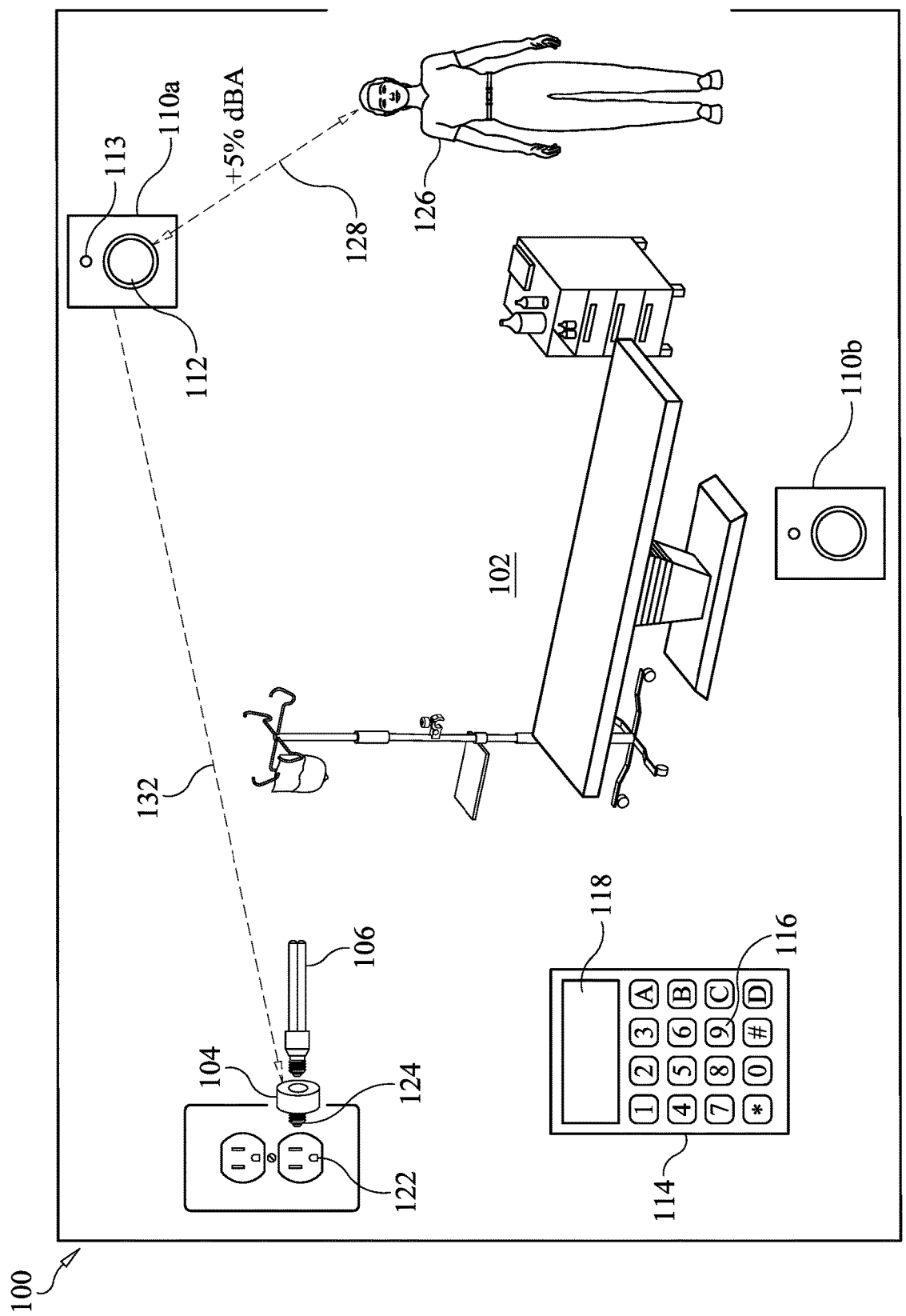
FIG. 2 illustrates a block diagram of the automated germicidal inhibitor system shown in FIG. 1, showing the sterilization mechanism operationally terminated upon detection of an event, in accordance with an embodiment of the present invention.

In some embodiments, the termination devices 110a-c may include a termination transceiver 500 and a sensor 112. As shown in FIG. 2, the sensor 112 is configured to detect an event 126. The event 126 is a sensory indication that a person, animal, or object is in the sterilization area 102. This forms the foundation for terminating operation of the sterilization mechanism 106 since it can be dangerous for the person to be exposed to the germicide element 108 from the sterilization mechanism 106. The termination devices 110a-c can be placed strategically throughout the sterilization area 102 to sense the entry points. Any number of termination devices 110a-c may be used.

In some embodiments, the event 126 can include motion, noise, temperature, and light. Thus, the motion can be the person entering the sterilization area 102. The noise can be a voice or footsteps from the person entering the sterilization area 102. The temperature can be the body temperature or the opening of lighting in the sterilization area 102, both of which indicate the presence of a person. Finally, the light can be an indication that the person has turned on the lights or has powered on other instruments in the sterilization area 102. However, the system 100 can utilize any event that is a physical indication that a person, animal, or object has entered into the sterilization area 102.

The event 126 is defined as occurring when the motion, the noise, the temperature, and the light, exceed an event threshold 128. In one non-limiting embodiment, the event 126 is triggered when the event threshold 128 exceeds the motion, the noise, the temperature, and the light, by about 5% above the normal. In one embodiment, the event threshold 128 is simply the motion, noise, temperature, and light levels in an empty, non-occupied sterilization area 102. Any of the motion, noise, temperature, and light that exceed this by 5%, (or more or less) represents exceeding the event threshold 128.

For example, an occupied doctor's office may have a noise decibel of 40-45 dBA. An empty doctor's office may have a noise decibel of 0-5 dBA. This shows at least 5% increase of noise when the doctor's office is occupied. Consequently, it would be advantageous for the event 126 to trigger the termination of the sterilization mechanism 106 when the office is occupied. In another embodiment, shown in FIG. 2, the event is simply a person entering the room, and the sensor 112 detecting motion therefrom. Thus, from zero motion in the sterilization area 102, to a human walking into the sterilization area 102, represents an exemplary 5% increase from the event threshold 128.

In some embodiments, the termination transceiver 500 is configured to transmit a termination signal 132 to the actuation transreceiver of the actuation device 104 when the event 126 is detected. The termination signal 132 commands the switch mechanism of the actuation device 104 to terminate operation of the sterilization mechanism 106. For example, a valve in the germicidal sprayer is turned to the "Off" position. In some embodiments, the termination signal 132 may include a radio frequency signal, or data packets. When the termination of the sterilization mechanism 106 occurs, all devices enter emergency mode, with red LED's, green LED's, and the audible alert mechanism illuminating and beeping to indicate termination of sanitization process.

In one non-limiting embodiment, the inhibitor device 110a comprises a standalone sensor/monitor devise with a radio frequency transceiver. The function of the inhibitor device is to sense the presence of a human by motion, noise, light; and transmits a radio frequency signal to the actuator device to pause the ultra violet light bulbs. When nothing is sensed, the ultra violet light bulbs resume its operation to finished the predetermine exposure dose. Several of these inhibitor devices can be mounted in the desired sterilization area 102 to safeguard it, one by the door entrance, one by the seats, once in the middle of the ceilings, etc., so that sensing can cover all possibilities.

In operation, the user initially couples the sterilization mechanism 106 to the actuation device 104. The actuation device 104 is then plugged into an external power source, such as an electrical socket. This can provide alternating current in one embodiment. The sterilization mechanism 106 is now powered transmit a germicide element 108. Next, the command device 114 is engaged by the user either directly or through a personal communication device.

Once it has been determined that the sterilization area 102 is empty, the user enters a code 120 into the entry key pad 116. This triggers an actuation signal which is transmitted from the command transreceiver to the actuation transreceiver (See FIG. 1). Consequently, the switch mechanism mechanically causes the sterilization mechanism 106 to emit the germicide element 108. This can be simply closing the electrical circuit to ultraviolet light source, or turning a switch in a germicidal composition sprayer.

At this point, the germicide element 108, whether ultraviolet light, or a spray germicide composition, is sterilizing the sterilization area 102. The one or more termination devices 110a, 110b maintain operation to detect motion, light, noise, or other physical elements that indicate a person, animal, or object has entered the sterilization area 102. Once the sensor 112 detects the event, the termination transceiver transmits a termination signal to the actuation transreceiver (See FIG. 2). Consequently, the switch mechanism mechanically causes the sterilization mechanism 106 to terminate emitting the germicide element 108. This can be simply opening an electrical circuit to ultraviolet light source, or turning a switch in a germicidal composition sprayer.

One non-limiting operational series of steps are as follows. The user enters a password on the command device 114 to activate the ultra violet light bulb. If the password is correct, the command device 114 sends a radio frequency actuation signal to all the actuator devices and inhibitor devices. The actuator devices and inhibitor devices flash a red LED, indicating the short wavelength ultra violet light has been activated. When the activation command is issued, the actuation device 104 turn on the ultra violet light for the activation predetermined time period, and turns it back off.

Simultaneously, the inhibitor devices 110a-c are monitoring the surrounding sterilization area 102, and if any of the sensors 112 detects abnormal values exceeding the event threshold, after receiving the actuation command 130, the corresponding inhibitor device 110a will send the inhibit signal 132 so that the actuator device 104 terminates operation of the sterilization mechanism 106. At this point, all devices enter emergency mode, with red LED's, green LED's, and the audible alert mechanism illuminating and beeping to indicate termination of sanitization.

However, when the event threshold 128 returns to within the 5% normal range, the inhibitor signal is ceased, and all devises will go back normal. The actuator device then resumes the activation time till the end. Normally all devises are flashing green LED's indicating they are on and ready. All the device may also flash red LED's when activities are reported. Further, both red and green LED's flash when entered a programing mode. And all the red LED's, green LED's, and the audible alert mechanism if there is an inhibit signal issued during activation period.

These and other advantages of the invention will be further understood and appreciated by those skilled in the art by reference to the following written specification, claims and appended drawings.

Because many modifications, variations, and changes in detail can be made to the described preferred embodiments of the invention, it is intended that all matters in the foregoing description and shown in the accompanying drawings be interpreted as illustrative and not in a limiting sense.

Thus, the scope of the invention should be determined by the appended claims and their legal equivalence.

What is claimed is:

1. An automated germicidal inhibitor system, the system comprising:
    a sterilization mechanism operable to emit a germicide element;
    an actuation device is detachably coupled to the sterilization mechanism, the actuation device comprising a plug operable to enables coupling to an external power outlet, whereby energy from the external power outlet powers the sterilization mechanism;
    the actuation device further comprising an actuation transreceiver and a switch mechanism, the actuation transreceiver and the switch mechanism are operatively connected to the sterilization mechanism, wherein the switch mechanism is operable to actuate operation of the sterilization mechanism;
    a command device comprising a command transceiver, an entry key pad, and a timer, wherein the entry key pad is operable to enable entry of a code, the timer is operable to count a predetermined time period, and the command transceiver is operable to transmit an actuation signal to the actuation transreceiver of the actuation device when the code is entered,
    whereby the actuation signal commands the switch mechanism to actuate operation of the sterilization mechanism; and
    one or more termination devices comprising a termination transceiver and a set of sensors, wherein the set of sensors are operable to detect an event, the termination transceiver is operable to transmit a termination signal to the actuation transreceiver of the actuation device when the event is detected and when the predetermined time period elapses,
    whereby the termination signal commands the switch mechanism of the actuation device to terminate operation of the sterilization mechanism.

2. The automated germicidal inhibitor system of claim 1, wherein the sterilization mechanism comprises an ultraviolet light tube.

3. The automated germicidal inhibitor system of claim 1, wherein the germicide element comprises a short-wavelength ultraviolet light.

4. The automated germicidal inhibitor system of claim 1, wherein the sterilization mechanism comprises a germicide sprayer.

5. The automated germicidal inhibitor system of claim 4, wherein the germicide element comprises a sanitization composition.

6. The automated germicidal inhibitor system of claim 1, wherein the plug comprises an electrical plug.

7. The automated germicidal inhibitor system of claim 1, wherein the switch mechanism comprises a bypass socket.

8. The automated germicidal inhibitor system of claim 1, wherein the switch mechanism includes at least one of the following: a static bypass switch, a maintenance bypass switch, UPS-mounted bypass switch, and an electrical bypass switch.

9. The automated germicidal inhibitor system of claim 1, wherein at least one of: the actuation device or the command device, comprise an MSP430 microcontroller.

10. The automated germicidal inhibitor system of claim 1, wherein the actuation device further comprises a digital display operable to display entry of the code into the entry key pad.

11. The automated germicidal inhibitor system of claim 1, wherein the actuation and termination signals comprise a radio frequency signal.

12. The automated germicidal inhibitor system of claim 1, wherein the code comprises a password.

13. The automated germicidal inhibitor system of claim 1, wherein the predetermined time period comprises a default value that is adjustable.

14. The automated germicidal inhibitor system of claim 1, wherein the event includes at least one of the following: motion, noise, temperature, and light.

15. The automated germicidal inhibitor system of claim 14, wherein the event occurs when at least one of: the motion, the noise, the temperature, and the light, exceed an event threshold.

16. The automated germicidal inhibitor system of claim 15, wherein the event occurs when at least one of: the motion, the noise, the temperature, and the light, exceed the event threshold by about 5 percent.

17. An automated germicidal inhibitor system, the system comprising:
- an ultraviolet light source operable to generate a short-wavelength ultraviolet light;
- an actuation device operatively connected to the ultraviolet light source, wherein the actuation device comprises an electrical plug operable to enable coupling to an external electrical outlet, whereby electricity from the external electrical outlet powers the ultraviolet light source,
- wherein the actuation device further comprises an actuation transreceiver and a socket bypass operable to actuate and terminate generation of the short-wavelength ultraviolet light by the ultraviolet light source;
- a command device comprising a command transceiver, an entry key pad, and a timer, wherein the entry key pad is operable to enable entry of a code, wherein the timer is operable to count a predetermined time period, and wherein the command transceiver is operable to transmit an actuation signal to the socket bypass when the code is entered,
- whereby the actuation signal actuates generation of the short-wavelength ultraviolet light by the ultraviolet light source; and
- one or more termination devices comprising a termination transceiver and a sensor, wherein the sensor is operable to detect an event, and the termination transceiver is operable to transmit a termination signal to the socket bypass when the event is detected and when the predetermined time period elapses,
- whereby the termination signal terminates generation of the short-wavelength ultraviolet light by the ultraviolet light source.

* * * * *